(12) United States Patent
Merkel et al.

(10) Patent No.: US 8,119,845 B2
(45) Date of Patent: *Feb. 21, 2012

(54) METHOD FOR PRODUCING 2-CHLORO-3,3,3,-TRIFLUOROPROPENE (HCFC-1233XF)

(75) Inventors: Daniel C. Merkel, Orchard Park, NY (US); Hsueh S. Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/880,951

(22) Filed: Sep. 13, 2010

(65) Prior Publication Data

US 2011/0004035 A1 Jan. 6, 2011

Related U.S. Application Data

(63) Continuation of application No. 12/179,055, filed on Jul. 24, 2008, now Pat. No. 7,795,480.

(60) Provisional application No. 60/951,796, filed on Jul. 25, 2007.

(51) Int. Cl.
*C07C 17/00* (2006.01)
(52) U.S. Cl. ...................................... 570/156
(58) Field of Classification Search .................. 570/156
See application file for complete search history.

(56) References Cited

U.S. PATENT DOCUMENTS

| | | | |
|---|---|---|---|
| 2,931,840 | A | 4/1960 | Marquis |
| 4,900,874 | A | 2/1990 | Ihara et al. |
| 6,013,846 | A | 1/2000 | Wismer et al. |
| 6,235,951 | B1 | 5/2001 | Sakyu et al. |
| 6,403,847 | B1 | 6/2002 | Nakada et al. |
| 7,795,480 | B2 * | 9/2010 | Merkel et al. .............. 570/155 |
| 2007/0197842 | A1 | 8/2007 | Mukhopadhyay et al. |

FOREIGN PATENT DOCUMENTS

| | | |
|---|---|---|
| JP | 09-194404 A | 7/1997 |
| WO | 98/12161 A1 | 3/1998 |
| WO | 00/17136 A1 | 3/2000 |
| WO | 2008/127940 A1 | 10/2008 |

OTHER PUBLICATIONS

Banks, et al., Preparation of 2,3,3,3-tetrafluoropropene from trifluoroacetylacetone and sulphur tetrafluoride; Journal of Fluorine Chemistry, vol. 82, Issue 2, pp. 171-174 (1997) GB.

* cited by examiner

*Primary Examiner* — Deborah D Carr
(74) *Attorney, Agent, or Firm* — Bruce Bradford

(57) ABSTRACT

The present invention relates to an improved method for manufacturing 2-chloro-3,3,3,-trifluoropropene (HCFC-1233xf) by reacting 1,1,2,3-tetrachloropropene, 1,1,1,2,3-pentachloropropane, and/or 2,3,3,3-tetrachloropropene with hydrogen fluoride, in a vapor phase reaction vessel in the presence of a vapor phase fluorination catalyst and stabilizer. HCFC-1233xf is an intermediate in the production of 2,3,3,3-tetrafluoropropene (HFO-1234yf) which is a refrigerant with low global warming potential.

20 Claims, No Drawings

METHOD FOR PRODUCING 2-CHLORO-3,3,3,-TRIFLUOROPROPENE (HCFC-1233XF)

CROSS-REFERENCE TO RELATED APPLICATION

This application is a continuing application of U.S. application Ser. No. 12/179,055, filed Jul. 24, 2008, which claims the priority benefit of U.S. Provisional Application No. 60/951,796, filed Jul. 25, 2007, which are incorporated herein by reference.

BACKGROUND

1. Field of the Invention

The present invention relates to a method for manufacturing hydrochlorofluoroolefins. More particularly, this invention relates to synthesis of 2-chloro-3,3,3,-trifluoropropene (HCFC-1233xf).

2. Description of Related Art

Fluorocarbon based fluids have found widespread use in industry in a number of applications, including as refrigerants, aerosol propellants, blowing agents, heat transfer media, and gaseous dielectrics. Because of the suspected environmental problems associated with the use of some of these fluids, including the relatively high global warming potentials associated therewith, it is desirable to use fluids having the lowest possible greenhouse warming potential in addition to zero ozone depletion potential. Thus there is considerable interest in developing environmentally friendlier materials for the applications mentioned above.

Tetrafluoropropenes, having essentially zero ozone depletion and low global warming potential, have been identified as potentially filling this need. However, the toxicity, boiling point, and other physical properties in this class of chemicals vary greatly, even between different isomers of a compound. One tetrafluoropropene having valuable properties is 2,3,3,3-tetrafluoropropene (HFO-1234yf). HFO-1234yf has been found to be an effective refrigerant, heat transfer medium, propellant, foaming agent, blowing agent, gaseous dielectric, sterilant carrier, polymerization medium, particulate removal fluid, carrier fluid, buffing abrasive agent, displacement drying agent and power cycle working fluid. Thus, there is a need for new manufacturing processes for the production of tetrafluoropropenes and in particular 2,3,3,3-tetrafluoropropene.

One process for producing tetrafluoropropenes involves the use of tetrachloropropenes as a reactant (U.S. 2007-0197842 A1). Additionally, several other methods of preparing hydrofluoroalkenes are known. For example, U.S. Pat. No. 4,900,874 (Ihara et al) describes a method of making fluorine containing olefins by contacting hydrogen gas with fluorinated alcohols. U.S. Pat. No. 2,931,840 (Marquis) describes a method of making fluorine containing olefins by pyrolysis of methyl chloride and tetrafluoroethylene or chlorodifluoromethane. The preparation of HFO-1234yf from trifluoroacetylacetone and sulfur tetrafluoride has been described. See Banks, et al., *Journal of Fluorine Chemistry*, Vol. 82, Iss. 2, p. 171-174 (1997). Also, U.S. Pat. No. 5,162,594 (Krespan) discloses a process wherein tetrafluoroethylene is reacted with another fluorinated ethylene in the liquid phase to produce a polyfluoroolefin product.

Notwithstanding prior teachings, applicants have come to appreciate a continuing need for methods of efficiently preparing intermediates of certain hydrohalocarbons, particularly compounds which are in part useful as intermediates in the preparation of tetrafluoropropenes, such as 2,3,3,3-tetrafluoropropene (HFO-1234yf).

The prior art discloses various processes for the preparation of polyhaloolefin products that involve separate steps as well as disparate reaction conditions, reagents, and catalysts. The efficiency of such multi-step processes is thus limited by the efficiency of each individual step. As such, one inefficient step may make the entire process more resource intensive, less effective at converting intermediates to the desired fluorocarbon products and less productive, suffering yield losses due to increased impurity formation.

The present invention offers a less resource-intensive process that produces increased conversion of intermediates to the end product polyhaloolefin over a longer period due to substantially increased catalyst life. This is achieved by Applicants' discovery of subjecting a tetrachloropropene to fluorination with a fluorinating agent and a catalyst in the presence of a stabilizer.

SUMMARY OF THE INVENTION

Applicants have discovered an improved method for producing a tetrahalopropene, such as 2-chloro-3,3,3,-trifluoropropene, that involves reacting one chlorocarbon or mixed chlorocarbon feed material selected from the group of 1,1,2,3-tetrachloropropene, 1,1,1,2,3-pentachloropropane (HCC-240db), and 2,3,3,3-tetrachloropropene with hydrogen fluoride, in a vapor phase reaction vessel and in the presence of a vapor phase fluorination catalyst and at least one stabilizer, and at conditions effective to produce the desired tetrahalopropene.

Preferably, the preferred contacting step produces a reaction product comprising tetrahalopropene, and in particular 2-chloro-3,3,3-trifluoropropene (HFO-1233xf). In preferred embodiments, the contacting step comprises reacting a tetrachloropropene and/or pentachloropropane with a fluorinating agent, such as HF, in the gas phase in the presence of at least one catalyst and at least one stabilizer. In a particularly preferred embodiment, the catalyst is $Cr_2O_3$ and the stabilizer is di-isopropyl amine. In certain preferred embodiments, the conversion of the tetrachloropropene is from about 70% to about 100% and the selectivity for HFO-1233xf is from about 50% to about 99%.

DETAILED DESCRIPTION OF PREFERRED EMBODIMENTS

One beneficial aspect of the present invention is that it enables the production of desirable haloolefins, preferably C3 haloolefins, without the inefficiency of short-lived catalyst underperformance. More specifically, certain preferred embodiments of the present invention involve producing the desired C3 haloolefins using the combination of at least one catalyst and at least one stabilizer. Applicants have discovered that the use of at least one stabilizer in conjunction with the catalyst component results in a significant improvement in catalyst longevity. In a preferred embodiment, catalyst longevity is improved by at least 43%, and more preferably by at least 50%. The resulting process is significantly more efficient and cost-effective as it thus uses reduced catalyst amounts and results in greater conversion of starting materials to the desired product.

Applicants have recognized that the production of one or more of the desired haloolefins, in particular hydrofluoropropenes, was inefficient due to unusually poor catalyst performance. By way of non-limiting explanation, as further detailed below, such poor performance may be the result of a side polymerization reaction or coking involving the catalyst. Applicants have also unexpectedly discovered that the presence of a stabilizer in the reaction mixture substantially prevents this polymerization or coking and, in a preferred embodiment, improves catalyst performance, preferably by at least 43%, more preferably by at least 50%, than that of reactions conducted with catalyst in the absence of stabilizer.

Preferably, 1,1,2,3-tetrachloropropene, 2,3,3,3-tetrachloropropene, or 1,1,1,2,3-pentachloropropane or mixture thereof is exposed to reaction conditions to produce a reaction product comprising 2-chloro-3,3,3,-trifluoropropene. Preferred embodiments of the preferred process are described below in non-limiting detail.

The methods of the present invention preferably comprise reacting one chlorocarbon or mixed chlorocarbon feed material selected from the group of 1,1,2,3-tetrachloropropene, 1,1,1,2,3-pentachloropropane (HCC-240db), and 2,3,3,3-tetrachloropropene with a fluorinating agent to produce a fluorinated haloolefin, preferably a C3 fluorinated haloolefin, more preferably 2-chloro-3,3,3,trifluoropropene (HFC-1233xf). This preferred reaction step may be described, by way of illustration but not necessarily by way of limitation, by the following reaction equation in connection with embodiments in which the tetrachloropropene is 1,1,2,3-tetrachloropropene and the fluorinating agent is hydrogen fluoride:

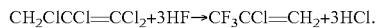

In certain preferred embodiments, the present converting step is carried out under conditions effective to provide a tetrachloropropene conversion of at least about 40%, more preferably at least about 55%, and even more preferably at least about 70%. In certain preferred embodiments the conversion is at least about 90%, and more preferably about 100%. Further in certain preferred embodiments, the conversion of the tetrachloroproene to produce a C3 haloolefin is conducted under conditions effective to provide a C3 haloolefin selectivity of at least about 85%, more preferably at least about 90%, and more preferably at least about 95%, and even more preferably about 100%.

In a particularly preferred embodiment, the invention relates to a continuous method for producing 2-chloro-3,3,3,-trifluoropropene (HCFC-1233xf) by vapor phase fluorination of one chlorocarbon or mixed chlorocarbon feed material selected from the group of 1,1,1,2,3-pentachloropropane (HCC-240db), 2,3,3,3-tetrachloropropene, and 1,1,2,3,-tetrachloropropene (HCC-1230xf) with hydrogen fluoride to produce a stream comprising hydrogen fluoride, 2-chloro-3,3,3,-trifluoropropene and hydrogen chloride.

This reaction may be conducted in any reactor suitable for a vapor or liquid phase fluorination reaction. Preferably the reactor is constructed from materials which are resistant to the corrosive effects of hydrogen fluoride and catalyst such as Hastalloy, Inconel, Monel and vessels lined with fluoropolymers. In case of a vapor phase process, the reactor is filled with a vapor phase fluorination catalyst. Any fluorination catalysts known in the art may be used in this process. Suitable catalysts include, but are not limited to chromium, aluminum, cobalt, manganese, nickel and iron oxides, hydroxides, halides, oxyhalides, inorganic salts thereof and their mixtures. Combinations of catalysts suitable for the present invention nonexclusively include $Cr_2O_3$, $FeCl_3/C$, $Cr_2O_3/Al_2O_3$, $Cr_2O_3/AlF_3$, $Cr_2O_3/carbon$, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. Chromium oxide/aluminum oxide catalysts are described in U.S. Pat. No. 5,155,082 which is incorporated herein by reference. Chromium (III) oxides such as crystalline chromium oxide or amorphous chromium oxide are preferred with amorphous chromium oxide being most preferred. Chromium oxide ($Cr_2O_3$) is a commercially available material which may be purchased in a variety of particle sizes. Fluorination catalysts having a purity of at least 98% are preferred. The fluorination catalyst is present in an excess but in at least an amount sufficient to drive the reaction.

The reactor is preheated to the fluorination reaction temperature while anhydrous HF is fed to the reactor. The stream containing the chlorocarbon feed material, for example the 1,1,2,3-tetrachloropropene, and a stabilizer is introduced into the reaction vessel next, which is maintained at the desired temperature. The 1,1,2,3,-tetrachloropropene (HCC-1230xf) and HF may be fed to the reactor at any convenient temperature and pressure. In a preferred embodiment either or both of the HCC-1230xf and the HF are pre-vaporized or preheated to a temperature of from about 30° C. to about 300° C. prior to entering the reactor. In another embodiment, the HCC-1230xf and HF are vaporized in the reactor. The HF and HCC-1230xf feeds are then adjusted to the desired mole ratio. The HF to HCC-1230xf mole ratio preferably ranges from about 3:1 to about 100:1; more preferably from about 4:1 to about 50:1 and most preferably from about 5:1 to about 20:1.

The vapor phase fluorination reaction is conducted at a preferred temperature ranging from about 80° C. to about 400° C.; more preferably from about 100° C. to about 350° C. and most preferably from about 200° C. to about 330° C. Reactor pressure is not critical and can be superatmospheric, atmospheric or under vacuum. The vacuum pressure can be from about 5 torr (0.0966 psig) to about 760 torr (14.69 psig). During the vapor phase fluorination reaction, HCC-1230xf and HF are reacted in a vapor phase in the presence of the fluorination catalyst. The reactant vapor is allowed to contact the fluorination catalyst for from about 1 to 120 seconds or more preferably from about 1 to 20 seconds. For purposes of this invention, "contact time" is the time required for the gaseous reactants to pass through the catalyst bed assuming that the catalyst bed is 100% void.

In the preferred embodiment, the process flow is in the down direction through a bed of the catalyst. Before each use, the catalyst is preferably dried, pre-treated and activated. It may also be advantageous to periodically regenerate the catalyst after prolonged use while in place in the reactor. Pretreatment can be done by heating the catalyst to about 250° C. to about 430° C. in a stream of nitrogen or other inert gas. The catalyst may then be activated by treating it with a stream of HF diluted with a large excess of nitrogen gas in order to obtain high catalyst activity. Regeneration of the catalyst may be accomplished by any means known in the art such as, for example, by passing air or air diluted with nitrogen over the catalyst at temperatures of from about 100° C. to about 400° C., preferably from about 200° C. to about 375° C., for from about 8 hours to about 3 days, depending on the size of the reactor.

Thus, it is contemplated that the present reaction may be performed using a wide variety of process parameters and process conditions in view of the overall teachings contained herein. However, it is preferred in certain embodiments that this reaction step comprises a gas phase reaction, preferably in the presence of catalyst and a stabilizer.

The present reaction also incorporates the use of at least one stabilizer. Applicants have discovered that the addition of at least one stabilizer to the reaction results in significantly increasing the longevity of the catalyst, preferably by at least 43%, more preferably by at least 50%. By way of non-limiting explanation, it is believed that the presence of the stabilizer substantially prevents the undesirable polymerization of the starting materials with the catalyst. In the absence of the stabilizer, the catalyst becomes ineffective after a period of several hours due to this polymerizing side-reaction.

Stabilizers suitable for use in the present reaction include those known for use in halogenation reactions, and in particular halogenation reactions involving alkanes, alkenes, and alkynes. In some embodiments, the stabilizer is selected from the group comprising p-tap(4-tert-Amylphenol), methoxy-hydroquinone, 4-methoxyphenol(HQMME), triethylamine, di-isopropyl amine, butylated hydroxy anisole (BHA), thymol and combinations thereof. In certain preferred embodiments, the stabilizer comprises an amine-based stabilizer. More preferably, the stabilizer comprises triethylamine, di-isopropyl amine or combinations thereof. Of course, combinations of two or more of any of these stabilizers, or other stabilizers not named here, may be used.

The stabilizer is preferably present in an amount less than 300 ppm, more preferably in an amount less than 100 ppm, and most preferably, in an amount less than 10 ppm. By way of non-limiting explanation, it is believed that minimization of stabilizer amounts reduces the potential deactivation of the catalyst.

In certain preferred embodiments, the present step of fluorinating a tetrachloropropene to produce a C3 haloolefin comprises contacting the tetrachloropropene with a fluorinating agent, preferably under conditions effective to provide a tetrachloropropene conversion of at least about 50%, more preferably at least about 55%, and even more preferably at least about 70%. In certain preferred embodiments the conversion is at least about 90%, and more preferably about 100%. Furthermore, in certain preferred embodiments, the present step of fluorinating a tetrachloropropene to produce a C3 haloolefin is conducted under conditions effective to provide a C3 haloolefin selectivity of at least about 5%, more preferably at least about 20%, more preferably at least about 50%, and even more preferably at least about 90%. In embodiments in which the compound of tetrachloropropene comprises $CH_2ClCCl=CCl_2$, and $CCl_3CHCl=CH_2$ the selectivity to HFO-1233xf is at least about 5%, more preferably at least about 20%, more preferably at least about 50%, and even more preferably at least about 99%.

EXAMPLES

Additional features of the present invention are provided in the following examples, which should not be construed as limiting the claims in any way.

Examples 1-2

These examples illustrate addition of hydrogen fluoride to $CH_2ClCCl=CCl_2$ in a gas phase reaction in the absence of a stabilizer, which is illustrated by the following reaction scheme:

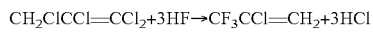
$CH_2ClCCl=CCl_2+3HF \rightarrow CF_3CCl=CH_2+3HCl$

A dual zone reactor was charged with 65 cc of pretreated $Cr_2O_3$ catalyst in the high temperature zone and 65 cc of 4 to 6 wt % $FeCl_3/C$ catalyst in the low temperature zone. The reactor was mounted inside a heater with two zones. The high temperature zone was maintained at 350° C. and the low temperature zone was maintained at 180° C. The organic feed ($CH_2ClCCl=CCl_2$) and hydrogen fluoride were fed via peristaltic pumps into the reactor at a rate of about 22 to about 27 g/hr and about 35 to about 45 g/hr, respectively, which resulted in a HF/organic mole ratio of about 14:1. The gas stream comprising the organic feed and HF was passed through the catalyst beds over a period of up to about 19 hours at a pressure of about 30 psig. The contact time through the $Cr_2O_3$ bed was about 6.4 seconds and the contact time through the $FeCl_3/C$ bed was about 8.8 seconds.

A GC and a GC/MS were used to analyze reactor effluent collected in separate product collection cylinders at the reactor exit line which contained deionized water to absorb the HF and HCl. The organic phase, containing the crude $CF_3CCl=CH_2$ (HFC-1233xf) product, was then isolated from the mixture by phase separation. In Table 1 below, Example 1 was reactor effluent material collected between 4 and 13 hours of run time. Also in table 1 below, Example 2 was reactor effluent material collected between 14 and 19 hours of run time. The total conversion of the organic feed was at least about 57% and the selectivity to HFC-1233xf was at least about 75%. The results are shown in Table I below.

TABLE I

|  | Example 1 | Example 2 |
| --- | --- | --- |
| % 1233xf produced | 59.9 | 45.45 |
| % byproduct produced | 18.6 | 11.9 |
| % organic feed converted | 78.5 | 57.35 |

Other byproducts produced include underfluorinated intermediates dichlorodifluoropropene (1232 isomer) and trichlorofluoropropene (1231 isomer) in addition to 1,2-dichloro-3,3,3-trifluoropropene (1223xd).

In Examples 1-2, the catalyst was observed to lose substantial activity at about 4 to 5 hours. Upon examination, the catalyst appeared to have fused together in the reactor such that it had to be removed via drilling. Applicants hypothesize that the observed catalyst fusion may be due to polymerization of the catalyst with the organic feed.

Example 3-5

These examples illustrate addition of hydrogen fluoride to $CH_2ClCCl=CCl_2$ in a gas phase reaction in the presence of a stabilizer.

The procedure of Examples 1-2 is repeated except that the pressure was maintained at about 20 psig, the HF/organic mole ratio was about 16:1, and 20 ppm of HQMME was added to the organic feed as a stabilizer. For Example 5, the reaction was run until catalyst deactivation, namely about 43 hours. The results are shown in Table 2 below.

TABLE II

|  | Example 3 | Example 4 | Example 5 |
| --- | --- | --- | --- |
| % 1233xf produced | 87.4 | 93.6 | 95.94 |
| % byproduct produced | ≈12.5 | ≈6 | ≈4 |
| % organic feed converted | 99.95 | 99.99 | 99.985 |

Other byproducts produced included underfluorinated intermediates dichlorodifluoropropene (1232 isomer) and trichlorofluoropropene (1231 isomer) as well as 1,2-dichloro-3,3,3-trifluoropropene (1223xd) and tetrafluoro-monochloropropane (such as HCFC-244bb).

In comparison with Examples 1-2 where no stabilizer was present, Examples 3-5 demonstrated significantly increased catalyst longevity. In particular, the catalyst was substantially functional even after over 40 hours of continuous use. In addition, the percent of organic feed converted increased from approximately 57% conversion to approximately 99% conversion with the addition of the stabilizer. In addition, when the catalyst was discharged from the reactor its physical appearance had not changed unlike the catalyst discharged during Examples 1-2. This demonstrates Applicants' discovery of the unexpectedly superior performance of a catalyst in the presently claimed reactions when used in conjunction with a stabilizer.

Examples 6-20

These Examples illustrate the stability testing of $CH_2ClCCl=CCl_2$ at different temperatures using different stabilizers in the presence of carbon steel, stainless steel and monel metal coupons. Each stabilizer was used in a concentration of 100 ppm and heated from room temperature to 100° C. and/or 150° C. Each stabilizer was then ranked according to the results, with the most poorly stable combinations receiving a rating of 1 and the most stable combinations at 150° C. receiving a rating of 10. The results are shown in Table III below.

TABLE III

| Stabilizer | Carbon steel | Stainless Steel | Monel |
| --- | --- | --- | --- |
| Thymol | 5 | 7 | 8 |
| Di-isopropyl Amine | 7 | 10 | 9 |
| Triethylamine | 7 | 8 | 10 |
| 4-tert-amyl-phenol | 1 | 9 | 5 |
| BHA | 1 | 6 | 5 |

Example 21

This Example illustrates the addition of hydrogen fluoride to $CH_2ClCCl=CCl_2$ in a gas phase reaction using di-isopropyl amine as a stabilizer with a relatively long catalyst contact time of about 2 seconds. A 1" monel pipe reactor was charged with 320 cc of fresh $Cr_2O_3$ catalyst at atmospheric pressure and at a temperature of 300° C. The organic feed ($CH_2ClCCl=CCl_2$) and hydrogen fluoride were fed via peristaltic pumps into the reactor at a rate of about 0.24 lb/hr and about 0.55 lb/hr, respectively, which results in a HF/organic mole ratio of about 20:1. The di-isopropyl amine stabilizer was added to the $CH_2ClCCl=CCl_2$ feed in an amount of 10 ppm. The gas stream comprising the organic feed, HF and stabilizer was passed through the catalyst bed over a period of up to about 85 hours. The contact time through the $Cr_2O_3$ bed was about 2.05 seconds.

Reactor effluent was analyzed as in Examples 1-2. After 85 hours of continuous run time, the total conversion of the organic feed was 100% and the selectivity to HFC-1233xf is at least about 90%. The catalyst showed no sign of deactivation or polymerization.

Example 22

This Example illustrates the addition of hydrogen fluoride to $CH_2ClCCl=CCl_2$ in a gas phase reaction using di-isopropyl amine as a stabilizer with a relatively long catalyst contact time of about 8 to about 10 seconds. A 2" monel pipe reactor was charged with 1800 cc of fresh $Cr_2O_3$ catalyst at atmospheric pressure and at a temperature starting at 200° C. and raised to 225° C. and then 250° C. The organic feed ($CH_2ClCCl=CCl_2$) and hydrogen fluoride were fed via peristaltic pumps into the reactor at a rate of about 0.35 lb/hr and about 0.78 lb/hr, respectively, which resulted in a HF/organic mole ratio of about 20:1. The di-isopropyl amine stabilizer was added to the $CH_2ClCCl=CCl_2$ in an amount of 10 ppm. The gas stream comprising the organic feed, HF and stabilizer was passed through the catalyst bed over a period of up to about 278 hours. The contact time through the $Cr_2O_3$ bed was about 8 to about 10 seconds.

Reactor effluent was analyzed as in Examples 1-2. After 278 hours of continuous run time, the total conversion of the organic feed was 100% and the selectivity to HFC-1233xf was at least about 80% to at least about 90%. The catalyst showed only minimal signs of deactivation over 278 hours of continuous run time, even with prolonged catalyst contact times.

Example 23

This example demonstrates the stability of a $Cr_2O_3$ catalyst during the following reaction:

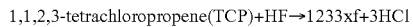

1,1,2,3-tetrachloropropene(TCP)+HF→1233xf+3HCl using 3 different TCP feeds. Run A used unstabilized TCP, while Run B used TCP stabilized with 13 ppm of p-tap, and Run C used TCP stabilized with 13 ppm of methoxy-hydroquinone. All three runs used a 1" reactor which was charged with 310 cc (about 448 grams) of freshly pretreated $Cr_2O_3$ catalyst. The catalyst bed hot spot reaction temperature for all the runs was kept in a range of 243-254° C. throughout the length of the experiment. Also, the same flow rates of HF and TCP were used for all the runs keeping the initial catalyst productivity and contact time the same for all 3 runs. All runs were performed at atmospheric pressure.

The average flow rate of HF for the experiments were 0.73 lb/hr and the average TCP flow rate was 0.43 lb/hr. The mole ratio of HF:TCP was about 15.3:1. The contact time for the experiments was about 1.5 seconds and the initial catalyst productivity (before catalyst deactivation) was about 25 lb/hr/ft³ catalyst. Results of the experiments are summarized in Table IV below. The use of stabilizer allowed the reaction to run a minimum of 43.3% longer than using unstabilized TCP.

TABLE IV

| TCP feed** | Catalyst Activity On-stream time (hrs)* | % improvement |
| --- | --- | --- |
| A | 44.5 | n/a |
| B | 63.75 | 43.3% |
| C | 66.75 | 50.0% |

*On-stream time was defined as the total amount of time the reaction was run until the conversion of TCP dropped below 75%.
**A = unstabilized TCP B = TCP stabilized with 13 ppm p-tap C = TCP stabilized with 13 ppm methoxy-hydroquinone

Having thus described a few particular embodiments of the invention, various alterations, modifications, and improvements will readily occur to those skilled in the art. Such alterations, modifications, and improvements, as are made obvious by this disclosure, are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A method of preparing fluorinated organic compounds comprising contacting at least one chlorocarbon selected from the group consisting of 1,1,2,3-tetrachloropropene, 2,3,3,3-tetrachloropropene, 1,1,1,2,3-pentachloropropane and combinations thereof with a halogenating agent in the presence of at least one catalyst and at least one stabilizer under conditions effective to produce a 2-chloro-3,3,3-trifluoropropene wherein the at least one stabilizer is selected from the group consisting of an amine stabilizer, a hydroquinone stabilizer, methoxy-hydroquinone, triethylamine, di-isopropyl amine, butylated hydroxy anisole (BHA), thymol and combinations thereof.

2. The method of claim 1 wherein said halogenating agent is a fluorinating agent.

3. The method of claim 2 wherein said fluorinating agent comprises hydrogen fluoride.

4. The method of claim 1 wherein at least a portion of said contacting step is conducted at a temperature of from about 80° C. to about 400° C.

5. The method of claim 1 wherein at least a portion of said contacting step is conducted at a pressure of from about 5 torr to about 150 psig.

6. The method of claim 1 wherein said contacting step comprises conducting at least a portion of said contacting step in the gas phase.

7. The method of claim 1 wherein said catalyst comprises at least one fluorination catalyst.

8. The method of claim 7 where the at least one fluorination catalyst is selected from the group consisting of $Cr_2O_3$, $FeCl_3/C$, $Cr_2O_3$ $Cr_2O_3/Al_2O_3$, $Cr_2O_3/AlF_3$, $Cr_2O_3/carbon$, $CoCl_2/Cr_2O_3/Al_2O_3$, $NiCl_2/Cr_2O_3/Al_2O_3$, $CoCl_2/AlF_3$, $NiCl_2/AlF_3$ and combinations thereof.

9. The method of claim 7 wherein at least one fluorination catalyst comprises $Cr_2O_3$.

10. The method of claim 1 wherein said stabilizer comprises an amine stabilizer.

11. The method of claim 10 wherein said stabilizer comprises triethylamine.

12. The method of claim 10 wherein said stabilizer comprises di-isopropyl amine.

13. The method of claim 1 wherein said stabilizer comprises a hydroquinone stabilizer.

14. The method of claim 13 wherein said stabilizer comprises methoxy-hydroquinone.

15. The method of claim 1 wherein the concentration of said stabilizer is less than about 300 ppm.

16. The method of claim 15 wherein the concentration of said stabilizer is less than about 100 ppm.

17. The method of claim 15 wherein the concentration of said stabilizer is about 10 ppm or less.

18. The method of claim 1 wherein said catalyst in the presence of said stabilizer is substantially operable for a greater period of time than said catalyst wherein said stabilizer is not present.

19. The method of claim 18 wherein said catalyst in the presence of said stabilizer is substantially operable at least about 40% longer than said catalyst wherein said stabilizer is not present.

20. The method of claim 18 wherein said catalyst in the presence of said stabilizer is substantially operable at least about 50% longer than said catalyst wherein said stabilizer is not present.

* * * * *